US008744605B2

(12) United States Patent  
Su et al.

(10) Patent No.: US 8,744,605 B2  
(45) Date of Patent: Jun. 3, 2014

(54) HANDHELD DEVICE WORKOUT COACH SYSTEM

(75) Inventors: Che-Wei Su, Taichung (TW); Chung-Chieh Chen, Taichung (TW); Wei-Lung Chen, Taichung (TW)

(73) Assignee: Cycling & Health Tech Industry R & D Center, Taichung (TW)

( * ) Notice: Subject to any disclaimer, the term of this patent is extended or adjusted under 35 U.S.C. 154(b) by 0 days.

(21) Appl. No.: 13/616,728

(22) Filed: Sep. 14, 2012

(65) Prior Publication Data

US 2014/0081434 A1    Mar. 20, 2014

(51) Int. Cl.  
     *G06F 19/00*      (2011.01)

(52) U.S. Cl.  
     USPC .......................................................... 700/91

(58) Field of Classification Search  
     USPC ................. 463/20–25, 42; 482/4, 8, 901, 910  
     See application file for complete search history.

(56) References Cited

U.S. PATENT DOCUMENTS

| 7,722,502 | B2 | 5/2010 | Holkkola |
| 7,846,067 | B2 | 12/2010 | Hanoun |
| 2003/0127636 | A1 * | 7/2003 | Piron .............................. 256/10 |
| 2010/0216600 | A1 * | 8/2010 | Noffsinger et al. ............... 482/5 |
| 2012/0094649 | A1 * | 4/2012 | Porrati et al. .............. 455/422.1 |
| 2012/0123883 | A1 * | 5/2012 | Charrat .......................... 705/17 |
| 2012/0129452 | A1 * | 5/2012 | Koh et al. .................... 455/41.1 |

* cited by examiner

*Primary Examiner* — Ronald Laneau  
(74) *Attorney, Agent, or Firm* — Muncy, Geissler, Olds & Lowe, P.C.

(57) ABSTRACT

A handheld device workout coach system includes: at least a handheld device installed therein with a coaching program and having a near field communication (NFC) module and a ID recognition data; at least a fitness device having a master control unit, a near field communication (NFC) module corresponding in position and function to the master control unit, and a platform; and a server stored therein with workout prescriptions downloadable by the at least a handheld device and available to the coaching program. The master control unit has an equipment recognition data. The handheld device and the fitness device get connected by near field communication (NFC) technology as soon as the handheld device is positioned on the platform of the fitness device and recognize each other to thereby execute the coaching program instantly and automatically, such that a corresponding one of the workout prescriptions instructs a user to take exercise.

10 Claims, 3 Drawing Sheets

HANDHELD DEVICE WORKOUT COACH SYSTEM

BACKGROUND OF THE INVENTION

1. Technical Field

The present invention relates to fitness devices, and more particularly, to a handheld device workout coach system for providing a fitness workout program by means of a fitness device operating in conjunction with a smart phone.

2. Description of Related Art

Gym users having a workout session in the gym usually use fitness devices in sequence in accordance with a fitness workout program recommended by a workout coach in hopes of achieving the goals and effects of fitness workout.

However, most gym users do not have sufficient financial resources to hire a personal coach who gives instant instructions; instead, after enrolling on a fitness workout course, gym users usually keep looking for a related fitness device independently throughout the fitness workout course. In such a situation, gym users judge or determine on their own whether they have done a workout sufficiently with a fitness device—for example, whether the workout duration is long enough, whether operation frequency is high enough, and whether a predetermined operation intensity is attained. If the gym users happen to be lazy or impatient with a lengthy workout, they will likely to reduce the operation frequency or shorten the workout duration, thereby failing to achieve the goals and effects of fitness workout or resulting in unsatisfactory effects of fitness workout.

U.S. Pat. No. 7,722,502 discloses: installing, into an exercise device, software configured to identify a user and to collect information on the exercise performance of the user; assigning a first identifier to the user of the exercise device; assigning a second identifier to the exercise device; and storing the user's exercise parameters in an accessible memory. However, U.S. Pat. No. 7,722,502 is about a RFID-based system that lacks a mechanism for use with the user's handheld device (such as a smart phone), and thus it does not involve the technical concept of personal coaches.

U.S. Pat. No. 7,846,067 discloses collecting a user's exercise data by a RFID tag, a microchip, or a magnetic means and sending the exercise data to a database. However, U.S. Pat. No. 7,846,067 does not disclose a mechanism for use with the user's handheld device.

The aforesaid prior art merely discloses the art of sending a data related to a user's status and a data related to the user's way of using a fitness device to a database, but does not disclose taking the initiative in giving advice or a reminder to a user in the same manner as a workout coach does.

SUMMARY OF THE INVENTION

It is an objective of the present invention to provide a handheld device workout coach system essentially comprising at least a handheld device, at least a fitness device, and a coaching program, such that the handheld device executes the coaching program to instruct a user to use a corresponding one of the fitness devices, thereby allowing the user to finish a workout program correctly in a way as if the user were given instructions by a personal workout coach.

In order to achieve the above and other objectives, the present invention provides a handheld device workout coach system comprising: at least a handheld device installed therein with a coaching program and an equipment parameter setting program and having a near field communication (NFC) module and a ID recognition data; at least a fitness device each having a master control unit, a near field communication (NFC) module connected to the master control unit and corresponding in position and function thereto, a platform, and at least a sensor connected to the master control unit, the master control unit having an equipment recognition data, wherein the handheld device is disposed on the platform, the near field communication (NFC) module having a near field communication (NFC) sensor disposed at the platform, and the at least a sensor being adapted to sense history of a user's operating the at least a fitness device; and a server connected to the at least a handheld device via a network system and stored therein with a plurality of workout prescriptions downloadable by the at least a handheld device and available to the coaching program, wherein, after the at least a handheld device has been positioned on the platform of the fitness device, the near field communication (NFC) module of the at least a handheld device gets connected to the near field communication (NFC) module of the fitness device, and the at least a handheld device identifies a current type of the fitness device by means of the equipment recognition data, whereas the fitness device recognizes the at least a handheld device by means of the ID recognition data, such that the at least a handheld device executes the coaching program instantly and automatically, thereby instructing the user to take exercise in accordance with a corresponding one of the workout prescriptions. Accordingly, the handheld device executes the coaching program to instruct the user to use the appropriate fitness device, such that the user can finish a workout program correctly in a way as if the user were given instructions by a personal workout coach.

In order to achieve the above and other objectives, the server is connected to the at least a fitness device rather than connected to the handheld device via a network system, and the server is stored therein with a plurality of workout prescriptions sent to the at least a handheld device via the at least a fitness device and adapted for use with the coaching program.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE EMBODIMENTS OF THE INVENTION

Figure 1:
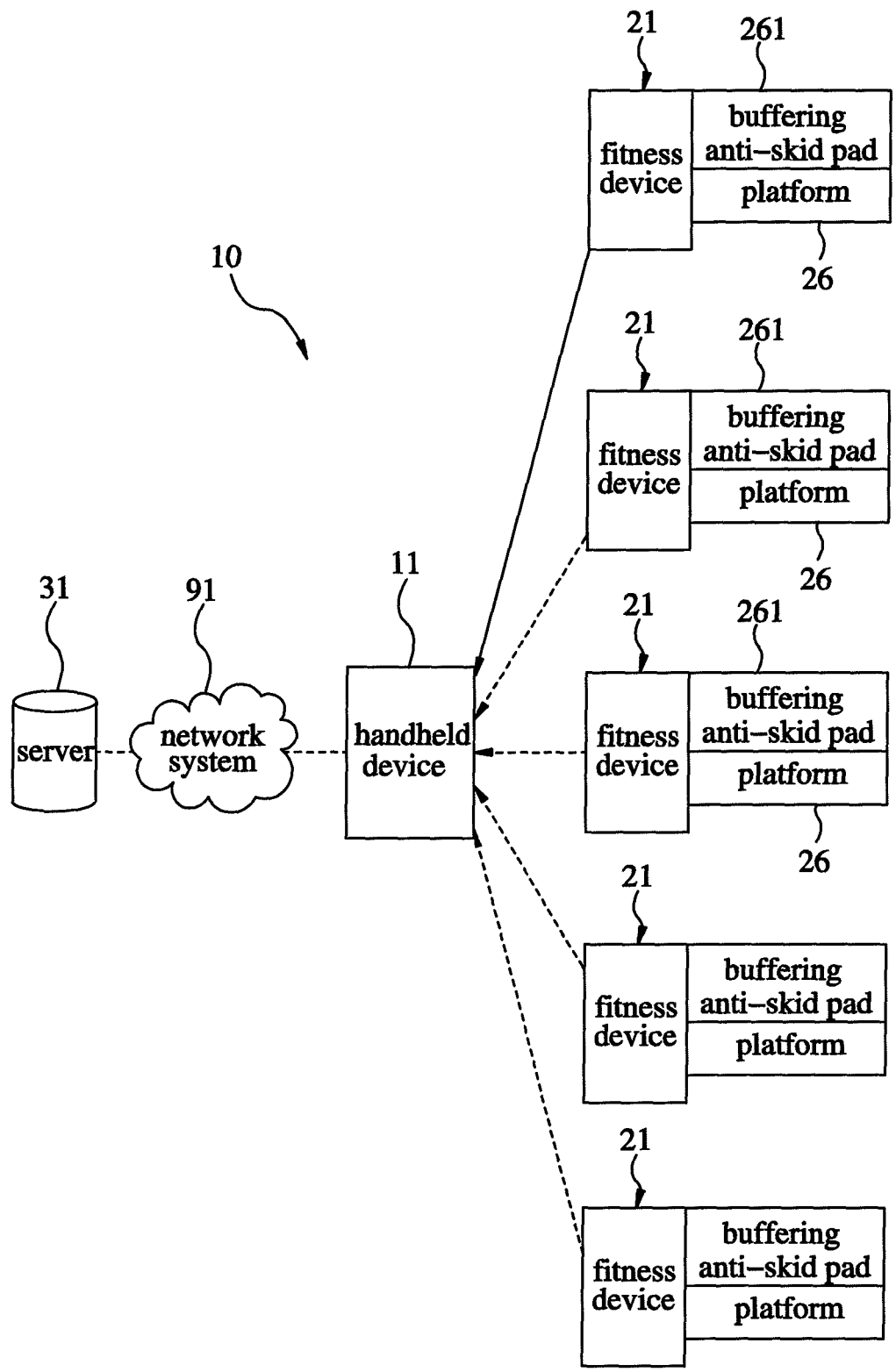
FIG. 1 is a structural schematic view of a handheld device workout coach system according to the first preferred embodiment of the present invention.
Figure 2:
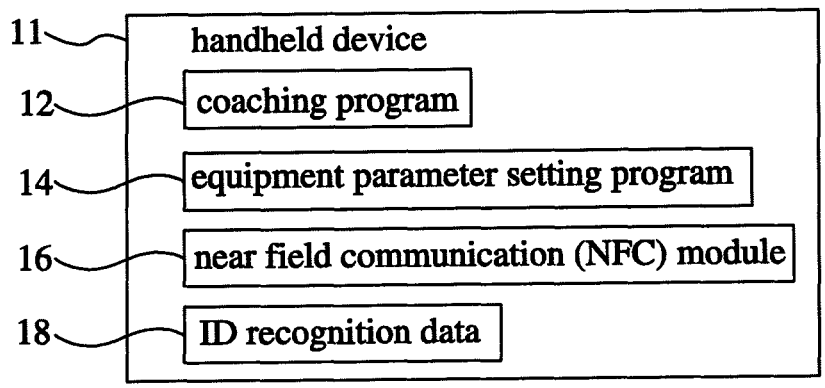
FIG. 2 is a structural schematic view of a portion of components of the handheld device workout coach system and a handheld device thereof according to the first preferred embodiment of the present invention.
Figure 3:
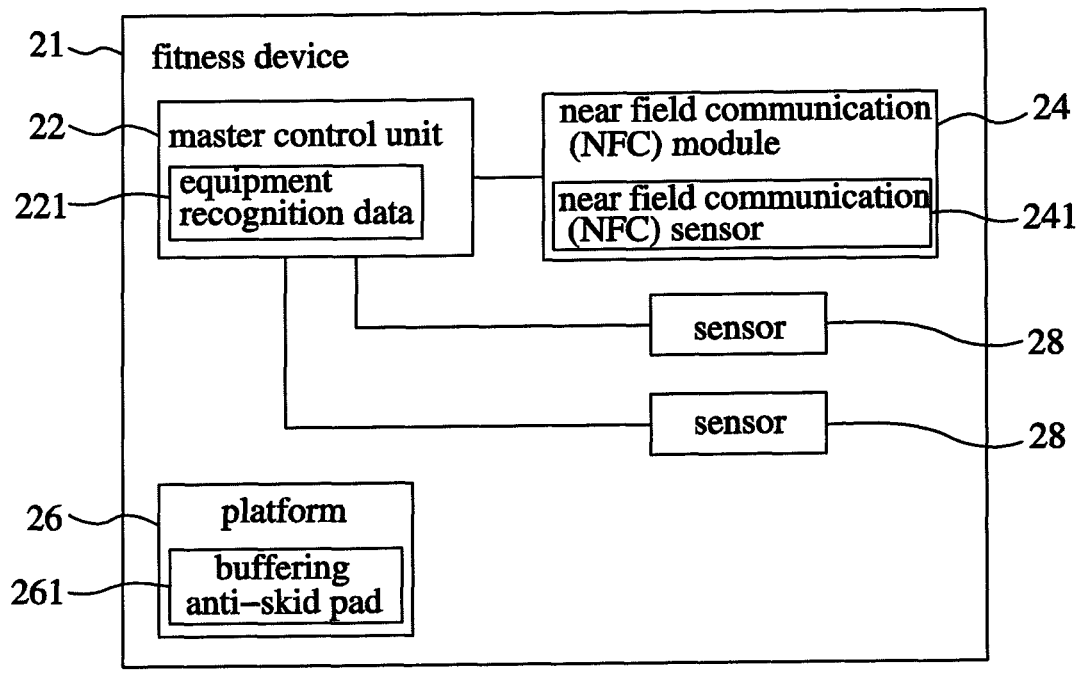
FIG. 3 is a structural schematic view of a portion of components of the handheld device workout coach system and a fitness device thereof according to the first preferred embodiment of the present invention.
Figure 4:
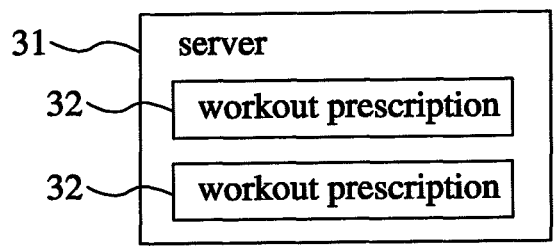
FIG. 4 is a structural schematic view of a portion of components of the handheld device workout coach system and a server thereof according to the first preferred embodiment of the present invention.

Referring to FIG. 1 through FIG. 4, the present invention provides in the first preferred embodiment thereof a handheld device workout coach system 10 essentially comprising at least a handheld device 11, at least a fitness device 21, and a server 31.

In this embodiment, the quantity of the at least a handheld device 11 is one to serve an exemplary purpose. A coaching program 12 and an equipment parameter setting program 14 are installed in the at least a handheld device 11. The handheld device 11 has a near field communication (NFC) module 16 and a ID recognition data 18. In this embodiment, the handheld device 11 is a smart phone, a tablet computer, or a personal digital assistant (PDA), and is exemplified by a smart phone. The near field communication (NFC) module 16 is built in any smart phone currently installed with an Android 4.0 operating system.

In this embodiment, the at least a fitness device 21 is exemplified by a variety of fitness devices, such as a treadmill, a chest expander, or a flywheel bicycle, wherein each type of the fitness device 21 comes in multiple different types of fitness devices with their respective functions. The aforesaid multiple-type fitness devices 21 each have a master control unit 22, a near field communication (NFC) module 24 corresponding in function to a near field communication (NFC) module 16 and connected to the master control unit 22, a platform 26, and at least a sensor 28 connected to the master control unit 22. The near field communication (NFC) module 24 corresponds in position and function to the master control unit 22. The master control unit 22 has an equipment recognition data 221. The handheld device 11 is disposed on the platform 26. The near field communication (NFC) module 24 has a near field communication (NFC) sensor 241 which is disposed at the platform 26 and adapted to sense whether a near field communication (NFC) module-enabled device is disposed on the platform 26. In this embodiment, as regards its quantity, the at least a sensor 28 is exemplified by a plurality of sensors and adapted to sense the history of a user's operating the multiple-type fitness devices 21.

In this embodiment, a buffering anti-skid pad 261 capable of buffering and preventing skid is disposed on the surface of the platform 26. Hence, once the handheld device 11 is positioned on the platform 26, the handheld device 11 will come into contact with the buffering anti-skid pad 261; as a result, the handheld device 11 is not only protected by the buffering effect of the buffering anti-skid pad 261, but is also prevented from sliding off the platform 26 by means of the anti-skid effect of the buffering anti-skid pad 261. However, the buffering anti-skid pad 261 is an optional component that provides an additional function rather than a required component. The buffering anti-skid pad 261 can be selectively dispensed with, if there is no need for buffering and skid prevention.

The server 31 is connected to the handheld device 11 via a network system 91. The server 31 stores therein a plurality of workout prescriptions 32 downloadable by the handheld device 11 and available to the coaching program 12. The workout prescriptions 32 each have at least a workout program. In this embodiment, the network system 91 is a local area network (LAN) or the Internet.

The near field communication (NFC) module 16 gets connected to the near field communication (NFC) module 24 as soon as the handheld device 11 is positioned on the platform 26 of the fitness device 21. The handheld device 11 identifies the current type of the fitness device 21 by means of the equipment recognition data 221, whereas the fitness device 21 recognizes the handheld device 11 by means of the ID recognition data 18, such that the handheld device 11 executes the coaching program 12 instantly and automatically, thereby instructing the user to take exercise in accordance with a corresponding one of the workout prescriptions 32. The history of the user's operating the multiple-type fitness devices 21 entails sending a result of the sensing of the sensors 28 to the handheld device 11 by the master control unit 22 of each said fitness device 21 through the connection of the near field communication (NFC) module 16 and the near field communication (NFC) module 24, and then sending the result from the handheld device 11 to the server 31. Accordingly, both the handheld device 11 and the server 31 can store data about the user's workout history; hence, in case the handheld device 11 is not connected to the server 31, the coaching program 12 can still arrange the next workout program set forth in the workout prescription 32 by making reference to the workout history. The user's workout history is not only stored in the server 31, but can also be available to the user independently by means of the handheld device 11.

The structure of the handheld device workout coach system in the first embodiment is described above. The operation of the handheld device workout coach system in the first embodiment is described below.

Prior to the commencement of its operation, the handheld device 11 has been installed therein with the coaching program 12 and the equipment parameter setting program 14, and the user has downloaded from the server 31 through a network connection the workout prescription 32 required for the handheld device 11 and adapted for use with the coaching program 12.

Referring to FIG. 1 through FIG. 4, to start operating the handheld device workout coach system 10, the user puts the handheld device 11 (exemplified by a smart phone) on the platform 26 of the fitness device 21 to thereby trigger spontaneous connection of the near field communication (NFC) module 16 of the handheld device 11 and the near field communication (NFC) module 24 of the fitness device 21; meanwhile, the handheld device 11 identifies the current type of the intended fitness device 21, whereas the fitness device 21 recognizes the handheld device 11.

Afterward, the coaching program 12 is automatically executed to thereby begin instructing the user to take exercise using an intended type of fitness devices in accordance with the current workout prescription 32. If the current fitness device 21 is exactly the intended fitness device, the user can begin taking exercise with the current fitness device 21 in accordance with the instruction of the coaching program 12. If the workout prescription 32 comprises workout programs of the multiple-type fitness devices 21, the coaching program 12 will instruct the user to take the next workout program with another fitness device 21 as soon as the user finishes taking a workout program of the first fitness device 21. The user may execute the equipment parameter setting program 14 with the handheld device 11, so as to configure a parameter related to the intended fitness device, such as load weight, speed, or frequency.

In this embodiment, near field communication (NFC) technology is applied, using a communication distance of just 10 cm approximately; hence, the connection is severed as soon as the user spaces the handheld device 11 apart from the platform 26 (by a distance that exceeds its communication distance.) Once the user puts the handheld device 11 on the platform 26 of another fitness device 21, the handheld device 11 will get connected to the new fitness device 21 by near field communication (NFC) technology to thereby identify and determine whether the current fitness device 21 is one which matches the workout prescription 32 being executed by the coaching program 12, and in consequence the coaching program 12 will send an instruction as needed.

As indicated above, in the first embodiment, the handheld device 11 executes the coaching program 12 to instruct the user to use the appropriate fitness device 21, such that the user can finish a workout program correctly in a way as if the user were given instructions by a personal workout coach.

Figure 5:
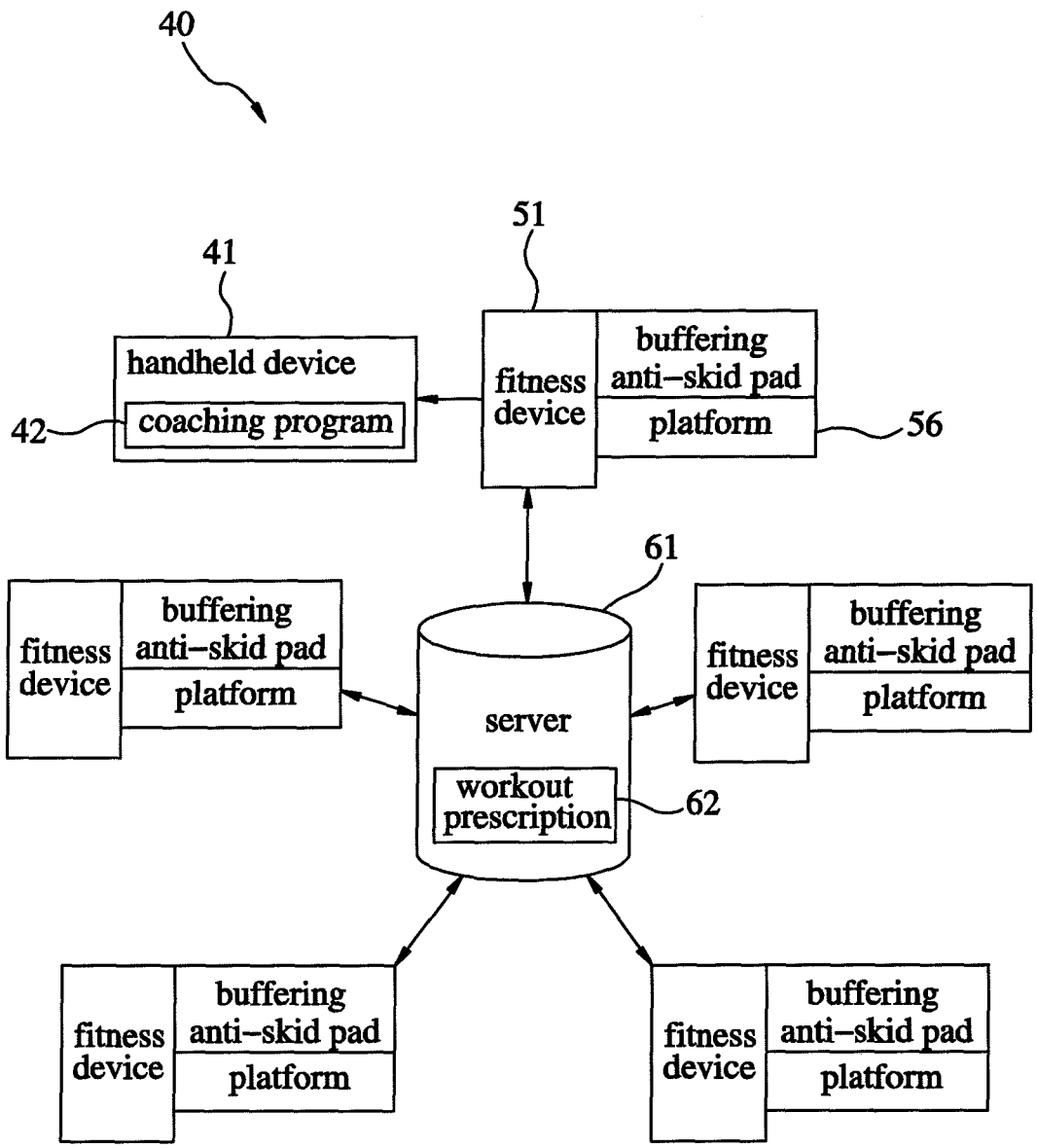
FIG. 5 is a structural schematic view of a handheld device workout coach system according to the second preferred embodiment of the present invention.

Referring to FIG. 5, there is shown a structural schematic view of a handheld device workout coach system 40 according to the second preferred embodiment of the present invention. The handheld device workout coach system 40 in the second embodiment is different from the handheld device workout coach system 10 in the first embodiment as follows:

A server 61 in the second embodiment is connected to the fitness devices 51 via the network system 91 rather than connected to the handheld device via the network system 91 in the first embodiment. A plurality of workout prescriptions 62 is stored in the server 61 and sent to the handheld device 41 via the fitness devices 51 for use with a coaching program 42 after the handheld device 41 has been positioned on a platform 56 of the fitness device 51 to form a connection of near field communication (NFC).

Furthermore, the history of the user's operating the fitness device 51 is not only sent to the handheld device 41 by the master control unit of the fitness device 51 through the connection of the near field communication (NFC) modules, but is also sent to the server 61 via the network system 91. Accordingly, both the server 61 and the handheld device 41 keep a record of the user's workout history.

The remaining structure and achievable functions and effects of the second embodiment are identical to that of the first embodiment and thus are not reiterated herein for the sake of brevity.

What is claimed is:

1. A handheld device workout coach system, comprising:
at least a handheld device installed therein with a coaching program and an equipment parameter setting program and having a near field communication (NFC) module and a ID recognition data, the at least one handheld device having a memory, the coaching program and the equipment parameter setting program being stored in the memory, the memory serving as a recording medium;
at least a fitness device each having a master control unit, a near field communication (NFC) module connected to the master control unit and corresponding in position and function thereto, a platform, and at least a sensor connected to the master control unit, the master control unit having an equipment recognition data, wherein the handheld device is disposed on the platform, the near field communication (NFC) module having a near field communication (NFC) sensor disposed at the platform, and the at least a sensor being adapted to sense history of a user's operating the at least a fitness device; and
a server connected to the at least a handheld device via a network system and stored therein with a plurality of workout prescriptions downloadable by the at least a handheld device and available to the coaching program,
wherein, after the at least a handheld device has been positioned on the platform of the fitness device, the near field communication (NFC) module of the at least a handheld device gets connected to the near field communication (NFC) module of the fitness device, and the at least a handheld device identifies a current type of the fitness device by means of the equipment recognition data, whereas the fitness device recognizes the at least a handheld device by means of the ID recognition data, such that the at least a handheld device executes the coaching program instantly and automatically, thereby instructing the user to take exercise in accordance with a corresponding one of the workout prescriptions.

2. The handheld device workout coach system of claim 1, wherein the at least a fitness device is of different types each being attributed to at least a fitness device and characterized by a unique fitness-related function.

3. The handheld device workout coach system of claim 1, wherein a buffering anti-skid pad capable of buffering and preventing skid is disposed on a surface of the platform of the at least a fitness device, wherein a near field communication (NFC) sensor of the near field communication (NFC) module is disposed beneath the buffering anti-skid pad.

4. The handheld device workout coach system of claim 1, wherein history of the user's operating the at least a fitness device entails sending a result of the sensing of the at least a sensor to the at least a handheld device by the master control unit through connection of the near field communication (NFC) module of the at least a handheld device and the near field communication (NFC) module of the at least a fitness device and then sending the result from the at least a handheld device to the server.

5. The handheld device workout coach system of claim 1, wherein the at least a handheld device is one of a smart phone, a tablet computer, and a personal digital assistant (PDA).

6. A handheld device workout coach system, comprising:
at least a handheld device installed therein with a coaching program and an equipment parameter setting program and having a near field communication (NFC) module and a ID recognition data, the at least one handheld device having a memory, the coaching program and the equipment parameter setting program being stored in the memory, the memory serving as a recording medium;
at least a fitness device each having a master control unit, a near field communication (NFC) module connected to the master control unit and corresponding in position and function thereto, a platform, and at least a sensor connected to the master control unit, the master control unit having an equipment recognition data, wherein the handheld device is disposed on the platform, the near field communication (NFC) module having a near field communication (NFC) sensor disposed at the platform, and the at least a sensor being adapted to sense history of a user's operating the at least a fitness device; and
a server connected to the at least a fitness device via a network system and stored therein with a plurality of workout prescriptions sent to the at least a handheld device via the at least a fitness device and adapted for use with the coaching program,
wherein, after the at least a handheld device has been positioned on the platform of the fitness device, the near field communication (NFC) module of the at least a handheld device gets connected to the near field communication (NFC) module of the fitness device, and the at least a handheld device identifies a current type of the fitness device by means of the equipment recognition data, whereas the fitness device recognizes the at least a handheld device by means of the ID recognition data, such that the at least a handheld device executes the coaching program instantly and automatically, thereby instructing the user to take exercise in accordance with a corresponding one of the workout prescriptions.

7. The handheld device workout coach system of claim 6, wherein the at least a fitness device is of different types each being attributed to at least a fitness device and characterized by a unique fitness-related function.

8. The handheld device workout coach system of claim 6, wherein a buffering anti-skid pad capable of buffering and preventing skid is disposed on a surface of the platform of the at least a fitness device, wherein a near field communication (NFC) sensor of the near field communication (NFC) module is disposed beneath the buffering anti-skid pad.

9. The handheld device workout coach system of claim 6, wherein history of the user's operating the at least a fitness device entails sending a result of the sensing of the at least a sensor to the at least a handheld device by the master control unit through connection of the near field communication (NFC) module of the at least a handheld device and the near field communication (NFC) module of the at least a fitness device and sending the result to the server via the network system.

10. The handheld device workout coach system of claim 6, wherein the at least a handheld device is one of a smart phone, a tablet computer, and a personal digital assistant (PDA).

* * * * *